United States Patent [19]

Dennis et al.

[11] Patent Number: 5,436,011
[45] Date of Patent: Jul. 25, 1995

[54] SOLID PHARMACEUTICAL DOSAGE FORM AND A METHOD FOR REDUCING ABRASION

[75] Inventors: Andrew B. Dennis; David L. McCann, both of Merseyside; Alexander P. Green, Hertfordshire, all of United Kingdom

[73] Assignee: Bristol-Myers Squibb Company, Princeton, N.J.

[21] Appl. No.: 48,692
[22] Filed: Apr. 16, 1993
[51] Int. Cl.⁶ ............................................. A61K 9/32
[52] U.S. Cl. ................................... 424/482; 424/465; 514/960; 427/2.14; 427/2.15; 427/2.18
[58] Field of Search ............... 424/480, 482, 497, 498; 427/2.14, 2.15, 2.18

[56] References Cited

U.S. PATENT DOCUMENTS

| | | | |
|---|---|---|---|
| 3,097,144 | 7/1963 | Banker | 424/481 |
| 3,149,039 | 9/1964 | Jeffries | 167/82 |
| 3,149,041 | 9/1964 | Jeffries | 167/82 |
| 3,379,554 | 4/1968 | Brindamour | 117/33 |
| 3,383,237 | 5/1968 | Tuerck | 117/105.1 |
| 3,533,804 | 2/1968 | Bennett | 424/6 |
| 3,629,394 | 2/1969 | Gaunt et al. | 424/441 |
| 3,751,277 | 8/1973 | Small et al. | 106/213 |
| 3,802,896 | 5/1974 | Westall et al. | 523/100 |
| 3,908,003 | 7/1974 | Ley et al. | 514/234.8 |
| 4,330,338 | 10/1978 | Banker | 106/197.2 |
| 4,423,027 | 12/1982 | Simon et al. | 424/479 |
| 4,482,387 | 11/1983 | Wood et al. | 106/270 |
| 4,520,009 | 11/1983 | Dunn | 514/161 |
| 4,629,620 | 7/1984 | Lindahl et al. | 424/473 |
| 4,687,660 | 8/1984 | Baker et al. | 424/465 |
| 4,775,536 | 2/1986 | Patell | 424/471 |
| 4,795,644 | 8/1987 | Zentner | 424/468 |
| 4,816,259 | 2/1987 | Matthews et al. | 424/463 |
| 4,857,337 | 5/1988 | Miller et al. | 424/480 |

FOREIGN PATENT DOCUMENTS

| | | |
|---|---|---|
| 4033064 | 8/1965 | Australia . |
| 8546934 | 9/1985 | Australia . |
| 8825946 | 11/1987 | Australia . |
| 609248 | of 0000 | Belgium . |
| 717236 | 12/1968 | Belgium . |
| 865633 | 4/1977 | Belgium . |
| 896483 | 4/1983 | Belgium . |
| 122463 | 3/1983 | European Pat. Off. . |
| 0133827 | 3/1985 | European Pat. Off. . |
| 238951 | 3/1986 | European Pat. Off. . |
| 0409432 | 1/1991 | European Pat. Off. . |
| 0572942 | 12/1993 | European Pat. Off. . |
| 1483990 | 5/1966 | France . |
| 2293438 | 12/1974 | France . |
| 1617328 | 7/1966 | Germany . |
| 2058163 | 12/1969 | Germany . |
| 2522483 | 5/1975 | Germany . |
| 3636123 | 10/1986 | Germany . |
| 43165 | 5/1964 | Ireland . |
| 815065 | 12/1962 | Japan . |
| 29369 | 1/1965 | Japan . |
| 7037796 | 3/1965 | Japan . |
| 2667769 | 7/1966 | Japan . |
| 2704069 | 12/1966 | Japan . |
| 7001076 | 8/1967 | Japan . |
| 179335 | 9/1975 | Japan . |
| 128512 | 10/1976 | Japan . |
| 095867 | 8/1977 | Japan . |
| 047058 | 4/1978 | Japan . |
| 134868 | 10/1978 | Japan . |
| 140349 | 10/1979 | Japan . |
| 124349 | 9/1980 | Japan . |
| 137936 | 10/1980 | Japan . |
| 149000 | 9/1981 | Japan . |
| 024534 | 2/1986 | Japan . |
| 051377 | 3/1986 | Japan . |
| 246391 | 10/1986 | Japan . |
| 161209 | 6/1987 | Japan . |
| 025341 | 2/1988 | Japan . |
| 6903248 | 11/1968 | Nigeria . |
| 624145 | 10/1961 | South Africa . |
| 650221 | 1/1964 | South Africa . |
| 655967 | 12/1964 | South Africa . |
| 8500209 | 7/1984 | South Africa . |
| 872146 | 1/1958 | United Kingdom . |
| 887682 | 10/1958 | United Kingdom . |
| 907309 | 2/1959 | United Kingdom . |
| 907310 | 2/1959 | United Kingdom . |
| 2025227 | 7/1978 | United Kingdom . |

*Primary Examiner*—Edward J. Webman
*Attorney, Agent, or Firm*—Ellen K. Park

[57] ABSTRACT

A method for reducing abrasion during film coating of susceptible solid dosage forms by applying to an uncoated dosage form, a subcoat containing a pharmaceutically acceptable polyalkylene glycol and the resulting solid pharmaceutical dosage form.

9 Claims, No Drawings

SOLID PHARMACEUTICAL DOSAGE FORM AND A METHOD FOR REDUCING ABRASION

BRIEF DESCRIPTION OF THE INVENTION

The present invention is directed to a method for reducing abrasion of a solid pharmaceutical dosage form by applying to an uncoated dosage form a subcoat comprising an amount of a pharmaceutically acceptable polyalkylene glycol sufficient to reduce abrasion, and to the resulting solid pharmaceutical dosage form.

DESCRIPTION OF THE INVENTION

In accordance with the present invention, a method is disclosed for reducing abrasion of a solid pharmaceutical dosage form subject to abrasion during the coating process. The process comprises applying to an uncoated dosage form a subcoat comprising an amount of a pharmaceutically acceptable polyalkylene glycol coating effective to reduce abrasion. The term "polyalkylene" refers to polymerized alkylenes, such as polyethylene, polypropylene and polybutylene.

The subcoat is applied from an aqueous solution which comprises about a 1 to 50% w/w or preferably 5 to 20% w/w of a polyalkylene glycol such as polyethylene glycol (PEG) having a molecular weight between about 4,000 to 10,000, preferably between about 6,000 to about 8,000. The amount of the subcoat is such that it is sufficient to reduce the abrasion compared to solid pharmaceutical dosage forms not having said subcoat. Abrasion as used hereto means any type of roughening or eroding of the surface of the solid dosage form. Generally, a dry weight of subcoat between 0.02% to about 0.5% w/w of the uncoated tablet is sufficient to reduce abrasion. Preferably, the dry weight of subcoat is about 0.1% w/w of the uncoated tablet.

Any conventional method of applying the subcoat may be utilized. For example the subcoat solution may be sprayed onto the solid pharmaceutical dosage form for between about 0.5 to 5 minutes. Other methods for applying the subcoat include fluid bed coating and a rotary granulator process. An exemplary method employing a conventional coating pan with baffles and conditions for applying the subcoat are as follows:

| | |
|---|---|
| Spray rate | 40–45 g/min |
| Total coating time | 2 to 10 min. |
| Solution volume | 90 to 150 mL |
| Drum rotation speed | 9 to 20 rpm |
| Air inlet temperature | 60–65° C. |
| Air exhaust temperature | 45–50° C. |

Once the subcoat has been applied, any other conventional coating for example, prolonged release, enteric coating and the like, may be applied as known in the art.

The subcoat is such that the absorption characteristics of the coated dosage form are substantially the same as those of the dosage form prior to coating.

The process of the instant invention is useful for tablets having an abrasive type nature such that the tablet surface roughens and erodes as the tablets are being coated. Examples of such tablets include formulations of verapamil, diflunisal, erythromycin and propranolol. However, it is within the scope of this invention that any solid dosage form prone to abrasion may be coated as disclosed herein to reduce abrasion prior to applying a conventional coat.

The following examples and preparations describe the manner and process of making and using the preferred embodiments of the invention and are illustrative rather than limiting. It should be understood that there may be other embodiments which fall within the spirit and scope of the invention as defined by the claims appended hereto.

Example 1

A 10% solution of a subcoat was prepared by mixing 0.1 kg of polyethylene glycol 8000 with 0.9 kg of purified water.

Example 2

Following the procedure of Example 1. a subcoat having the below ingredients was prepared:

| | |
|---|---|
| Polyethylene glycol 6000 | 0.1 kg |
| Purified water | 0.9 kg |

Example 3

Following the procedure of Example 1, a subcoat having the below ingredients was prepared:

| | |
|---|---|
| Polyethylene glycol 4000 | 0.1 kg |
| Purified water | 0.9 kg |

Example 4

Following the procedure of Example 1, a subcoat having the below ingredients was prepared:

| | |
|---|---|
| Polyethylene glycol 8000 | 0.15 kg |
| Purified water | 0.85 kg |

Example 5

Following the procedure of Example 1, a subcoat having the below ingredients was prepared:

| | |
|---|---|
| Polyethylene glycol 8000 | 0.20 kg |
| Purified water | 0.80 kg |

Example 6

A tablet having the below composition was coated with the subcoat of Example 1 such that the coating was about 0.1% w/w (dry) of the tablet:

| COMPOSITION | AMOUNT mg/tablet |
|---|---|
| Verapamil hydrochloride USP | 80.0 |
| Lactose N.F. | 35.8 |
| Microcrystalline cellulose (Avicel PH101) | 110.0 |
| Povidone USP (Polyvinylpyrollidone K30) | 3.0 |
| Croscarmellose sodium, NF, type A (Ac-Di-Sol) | 10.0 |
| Magnesium stearate N.F. | 1.2 |
| Total (dry weight) | 240.0 |

This subcoat was applied using the following coating conditions:

| | |
|---|---|
| Inlet air temperature | 60° C. |

-continued

| | |
|---|---|
| Exhaust air temperature | 50° C. |
| Bed temperature | 45° C. |
| Drying air volume | 5.1 m³/min |
| Atomizing air pressure | 60 psi |
| Spray rate | 40 g min$^{-1}$ |
| Tablet load | 9 kg |

Example 7

The tablets having the below compositions were coated with the subcoat of Example 2 such that the coating was about 0.1% w/w (dry) of the tablet:

| | AMOUNT mg/tablet | |
|---|---|---|
| COMPOSITION | 250 mg | 500 mg |
| Diflunisal USP | 250.00 | 500.00 |
| Pregelatinized starch 1500 NF | 89.00 | 178.00 |
| Sodium starch glycollate NF | 8.00 | 16.00 |
| Microcrystalline cellulose NF | 40.00 | 80.00 |
| Hydroxypropyl cellulose NF (Klucel EF) | 8.00 | 16.00 |
| Magnesium stearate NF | 5.00 | 10.00 |
| Total (dry weight) | 400.00 | 800.00 |

What is claimed is:

1. A method for reducing abrasion of a tablet dosage form subject to abrasion during coating, comprising applying to an uncoated dosage form a subcoat consisting of an amount of a pharmaceutically acceptable polyalkylene glycol coating effective to reduce abrasion.

2. The method as recited in claim 1, wherein the drug release characteristics of the coated tablet including the subcoat are the same as the tablet dosage form without the subcoat.

3. The method as recited in claim 1, whereto the polyalkylene glycol is polyethylene glycol.

4. The method as recited in claim 3, wherein the polyethylene glycol has a molecular weight of between about 6,000 to about 8,000.

5. The method as recited in claim 1, wherein the polyalkylene glycol has a molecular weight of between about 4,000 to 10,000.

6. The method as recited in claim 5, wherein the molecular weight is between about 6,000 to about 8,000.

7. The method as recited in claim 1, wherein the polyalkylene glycol is applied as an aqueous solution.

8. The method as recited in claim 7, wherein the subcoat comprises about a 1 to 50% w/w aqueous solution of the polyalkylene glycol, 9. The method as recited in claim 8, wherein the subcoat comprises about a 5 to 20% w/w aqueous solution of the pglyalkylene glycol.

* * * * *